United States Patent [19]
Horesh et al.

[11] Patent Number: 6,091,843
[45] Date of Patent: Jul. 18, 2000

[54] METHOD OF CALIBRATION AND REAL-TIME ANALYSIS OF PARTICULATES

[75] Inventors: Nadav Horesh, Petah Tikva; Danny S. Moshe, Kiryat Ono, both of Israel

[73] Assignee: Greenvision Systems Ltd., Tel Aviv, Israel

[21] Appl. No.: 09/146,361

[22] Filed: Sep. 3, 1998

[51] Int. Cl.[7] .............................. G06K 9/00; G06K 9/62; G01N 21/64
[52] U.S. Cl. ...................... 382/133; 382/128; 382/224; 250/461.1; 356/318; 435/4
[58] Field of Search ................................. 382/128, 133, 382/165, 224, 156, 203, 219; 250/458.1, 461.1; 356/318; 435/4, 6, 7.23

[56] References Cited

U.S. PATENT DOCUMENTS

| | | | |
|---|---|---|---|
| 5,257,182 | 10/1993 | Luck et al. | 382/224 |
| 5,287,272 | 2/1994 | Rutenberg et al. | 382/224 |
| 5,733,721 | 3/1998 | Hemstreet, III et al. | 435/6 |
| 5,798,262 | 8/1998 | Garini et al. | 435/287.2 |
| 5,872,859 | 2/1999 | Gur et al. | 382/224 |
| 5,880,830 | 3/1999 | Schechter | 356/318 |
| 5,978,497 | 11/1999 | Lee et al. | 382/224 |

Primary Examiner—Matthew Bella
Attorney, Agent, or Firm—Mark M. Friedman

[57] ABSTRACT

A method of analyzing particles for chemical or biological species. Spectral images of the particles are acquired. Targets are identified in the images and are classified according to morphology type and spectrum type. Each target is assigned a value of an extensive property. A descriptor vector is formed, each element of the descriptor vector being the sum of the extensive property values for one target class. The descriptor vector is transformed to a vector of mass concentrations of chemical species of interest, or of number concentrations of biological species of interest, using a relationship determined in a calibration procedure. In the calibration procedure, spectral images of calibration samples of known composition are acquired, and empirical morphology types and spectrum types are inferred from the spectral images. Targets are identified in the spectral images, classified according to morphology type and spectrum type, and assigned values of an extensive property. For each calibration sample, a calibration descriptor vector and a calibration concentration vector is formed. A collective relationship between the calibration descriptor vectors and the calibration concentration vectors is found, either by multivariate analysis or by training a neural network.

23 Claims, 6 Drawing Sheets

METHOD OF CALIBRATION AND REAL-TIME ANALYSIS OF PARTICULATES

FIELD AND BACKGROUND OF THE INVENTION

The present invention relates to chemical analysis and, more particularly, to on-line quantitative analysis of chemical species in particulates. In particular, the present invention relates to the on-line quantitation of polycyclic aromatic hydrocarbons (PAH) and other fluorescent contaminants in aerosols.

PAH are among the many organic materials that are commonly encountered as trace-level environmental contaminants in effluents associated with incomplete combustion, pyrolysis and other thermal degradation processes. The PAH family, defined as containing hydrocarbon species with three or more fused aromatic rings, includes many compounds suspected of being potent carcinogens. Therefore, identification and determination of emission levels of PAH is important in environmental assessment. Moreover, emission monitoring of PAH compounds is of considerable industrial importance as well, since several industrial processes can be controlled by a fast feedback of PAH composition and concentration.

Several procedures, such as gas chromatography/mass spectrometry (GC-MS), have been developed and applied for obtaining compound specific information for evaluation of PAH contamination. These procedures cannot be applied directly to particulate PAH analysis, because they all involve several sample preparation steps in which the particles are destroyed. The GC-MS methods, in particular, are complicated and expensive; they require state of the art high vacuum equipment and extensive investment of expert analyst's time. It is not cost effective to apply them routinely to samples that may not, in fact contain any relevant levels of PAH. Moreover, the GC-MS methods are not on-line methods for particulate analysis, and cannot be used for obtaining fast feedback which is required for both environmental protection and for industrial process control.

PAH compounds are produced primarily as a result of incomplete combustion of organic matter, and thus are believed to exist in both the vapor phase and the solid phase, as an integral constituent of particulate matter. Because the concentration of such pollutants in most atmospheric samples is very low, and because they are often associated with other contaminants, the identification and quantification of PAH are usually complex, time consuming and often inaccurate because of multistep isolation and determination techniques. This problem is primarily associated with analysis of PAH on aerosol particles, which is considered the most complicated task for classical methods of PAH analysis.

Nevertheless, analysis of PAH on aerosols is of intense interest to both industry and governmental environmental protection bodies. It has been proven that most PAH mass is found onto aerosol particles, rather than in the vapor phase. (This is because of the low vapor pressure of many of these compounds at ambient temperature.) The distribution of PAH as a function of aerodynamic diameter, for coke oven emission, shows that most contamination is associated with particles of diameter of 1–10 $\mu$m. The absolute concentration of PAH compounds an air is compound-dependent, and is usually in the range of 0.02–0.2 $\mu$g m$^{-3}$. Absolute concentration in the vicinity of industrial sites may be ten times higher, and concentrations in the $\mu$g m$^{-3}$ and higher, of particles having diameters between 10 and 100 $\mu$m or more, have been measured close to combustion chimneys.

Most of the currently employed analytical methods for PAH on aerosols involve (a) collection of particulate PAH by drawing a large volume of air through a filter, (b) extraction of the PAH collected on a filter paper with an organic solvent, and (c) chromatographic cleanup and separation followed by (d) identification and quantitation using one or a combination of spectroscopic and chromatographic methods, or mass spectrometry analysis in a high vacuum chamber.

There are a number of analytical difficulties associated with these traditional methods. The real-time analysis of PAH present in ambient air (fumes, coke oven emission, smoke or other gaseous media) cannot be achieved, mainly because of lack of selectivity, sensitivity, and mobility of the analytical instrumentation. Considering the above difficulties, and taking into account that traditional methods do not provide on-line and in-situ results, it follows that there is a widely recognized need for, and it would be highly advantageous to have, a method for real-time, on-line analysis of aerosol particles for PAH.

SUMMARY OF THE INVENTION

According to the present invention there is provided a method of analyzing particles for a plurality of species, including the steps of: (a) providing: (i) a plurality of morphology types; (ii) a plurality of spectrum types; (iii) a plurality of target classes, each of the target classes corresponding to one of the morphology types and one of the spectrum types, and (iv) a relationship between a descriptor vector and a concentration vector, the descriptor vector including a plurality of elements, each element of the descriptor vector corresponding to a different one of the target classes, the concentration vector including a plurality of elements, each element of the concentration vector corresponding to a different one of the species; (b) acquiring a plurality of images of the particles, each of the images being acquired at a different wavelength; (c) inferring the descriptor vector from the plurality of images; and (d) using the relationship to infer the concentration vector from the descriptor vector.

The present invention is a method of quantification of species on particles. The species may be either chemical species, such as PAH, or biological species, particularly microorganisms such as bacteria and algae. In the latter case, the microorganism itself may be the particle.

For definiteness, the description below focuses on the use of the present invention for the quantitation of PAH in aerosol particles. Therefore, in the description below, the images are of fluorescent or phosphorescent light emitted by the particles, under excitation by incident ultraviolet light, rather than of light reflected or transmitted by the particles. Nevertheless, the scope of the present invention includes the analysis of images of light reflected or transmitted by the particles, in addition to the analysis of light emitted by the particles in response to excitation. Furthermore, the excitation may be by incident electromagnetic radiation of any suitable wavelength, notably visible and infrared light, or even by simply heating the particles.

The particles to be analyzed are spread out on a two-dimensional surface, so that each pixel in each two dimensional intensity image represents a part of only one article. Generally, aerosol particles collected on the surface of a filter, as in the prior rt method of PAH analysis, are spread out appropriately. When the images are of light emitted by the particles in response to incident light, there are two general methods of acquiring the images. In the first method, the surface to be imaged is irradiated homogeneously, and the emitted light is transferred, via a suitable optical system, to a spectroscopic imaging device. Examples of such devices are the acousto-optic tunable filter and the scanning interferometer described by Lewis et al. in U.S. Pat. No. 5,377,003, which is incorporated by reference for all purposes as if fully set forth herein; the scanning interferometer described by Cabib et al. in U.S. Pat. No. 5,539,517 and produced by Applied Spectral Imaging, Ltd. of Migdal Haemek, Israel, under the name "ASI SD2000", and the liquid crystal tunable filter described in Fluorescence Imaging Spectroscopy and Microscopy (Xue Feng Wang & Brian Herman, editors, John Wiley & Sons, Inc., 1996). In the second method, the surface to be imaged is scanned using a focused beam of light, and the emitted light is analyzed by a conventional spectrometer. Under both methods, the spectrally decomposed emitted light is imaged by one of several methods. The straightforward method uses a solid-state area image sensor array such as an array of charge coupled detectors (CCD), with each detector of the array acquiring one pixel of each image. Another method is to acquire each image one row of pixels at a time using a scanning diode array. CCD arrays recently have become available that are sufficiently dense that several images corresponding to several different wavelengths can be acquired simultaneously. For example, a 4096×4096 CCD array can acquire 64 512×512 images simultaneously, at 64 different wavelengths. As an alternative to the spectrometers, these large CCD arrays can be used with a large number (64 in the example given) of narrow band optical filters to obtain single-wavelength images. Under this alternative, the sample must be moved, for example on a piezoelectric stage, from one filter to another. In the analysis of aerosol particles for PAH, the optical system includes a microscope, so that the final single-wavelength images are sufficiently magnified to resolve the target particles at the desired resolution of one or more pixels per particle.

The output of the image acquisition is, for each imaged portion of the two-dimensional surface, a set of images, each image at a different wavelength. These images are digitized and analyzed by standard image processing methods to produce, for each imaged portion of the two-dimensional surface, spectral images of targets. Typically, each target corresponds to one particle, or, in the case of images of PAH fluorescence, the portion of the surface of the particle occupied by one PAH species. Each target is classified as belonging to one of a standard set of morphology types and one of a standard set of spectrum types. For each target, a value of an extensive property, such as area or total intensity, is obtained. These values are summed separately for each target class. The array of summed extensive properties constitutes a collective descriptor vector for all the targets. A relationship is provided that relates the descriptor vector to a vector of concentrations of species of interest. If the species of interest are chemical species, then the concentrations are expressed as mass per unit area. If the species of interest are biological species, then the concentrations are expressed as number of organisms per unit area. This relationship is used to infer the concentrations of the species of interest from the descriptor vector.

The set of standard morphology types, the set of standard spectrum types, and the relationship between descriptor vectors and concentration vectors are obtained by a calibration procedure. A set of calibration samples is provided. These calibration samples may be collections of particles of known composition or collections of particles of unknown composition but of the type that is to be analyzed. For each calibration sample, one or more sets of images at different wavelengths are acquired. Each image includes a plurality of pixels. With each pixel is associated an intensity value. The set of intensity values of pixels that have a common location in the images of one set constitute a spectrum associated with that location. Spectra whose summed intensity exceeds a predetermined threshold are classified by cluster analysis to obtain the standard spectrum types. See, for example, R. L. Kettig and D. Landgrebe, "Classification of multispectral image data by extraction and classification of homogeneous objects", *IEEE Transactions on Geoscience Electronics*, Vol. GE14 p. 19 (1976). Locations whose summed intensity exceeds the threshold are grouped into calibration targets. For each calibration target, values of morphological parameters such as area or aspect ratio is calculated. The values of the morphological parameters are classified by cluster analysis to obtain the standard morphology types. Each calibration target also is classified as belonging to one of the standard spectrum types. For each calibration target, a value of an extensive parameter is obtained, and these values are summed to provide a calibration descriptor vector for each, as described above.

The calibration samples now are analyzed by a prior art method, if necessary, to obtain, for each calibration sample, a calibration concentration vector, each element of which is a value of the concentration of a species of interest in the calibration sample. The desired relationship between the calibration descriptor vectors and the calibration concentration vectors now is determined by standard computational methods, for example multivariate analysis or by training a neural net. The output of multivariate analysis is a linear transformation, expressed as a matrix, that relates descriptor vectors to corresponding concentration vectors. The descriptor vector is multiplied by this matrix to yield the concentration vector. The output of the training of a neural net is a trained neural net whose inputs are descriptor vectors and whose outputs are corresponding concentration vectors.

With regard to analysis of chemical species, the present invention is similar to the method of particulate analysis described in co-pending U.S. patent application Ser. No. 08/790,696. The significant differences between the present invention and U.S. Ser. No. 08/790,696 are as follows:

1. In U.S. Ser. No. 08/790,696, the spectra in the database are spectra of pure chemical species. In the present invention, the standard spectra are determined empirically in the calibration procedure. This is important in the case of PAH adsorbed on aerosols, because the spectra of adsorbed chemical species in general and of PAH in particular are known to be altered by the surfaces on which they are adsorbed and by contaminants.

2. In U.S. Ser. No. 08/790,696, the shapes of the particles are considered along with the spectra of the particles, but only in an ad hoc manner. In the present invention, the relationship between the descriptor vector and the concentration vector accounts explicitly and simultaneously for both morphologies and empirically determined spectra. This is particularly important in the case of PAH adsorbed on aerosols, because the fluorescence spectra of PAH crystals are known to depend on crystal morphology in general and crystal size in particular.

BRIEF DESCRIPTION OF THE DRAWINGS

The invention is herein described, by way of example only, with reference to the accompanying drawings, wherein.

DESCRIPTION OF THE PREFERRED EMBODIMENTS

The present invention is of a method of quantitative analysis of chemical species in particulates which is based on an empirically determined relationship among spectra, morphologies and concentrations. Specifically, the present invention can be used for real-time, on-line quantification of PAH in aerosols.

The principles and operation of particulate analysis according to the present invention may be better understood with reference to the drawings and the accompanying description.

Figure 1:
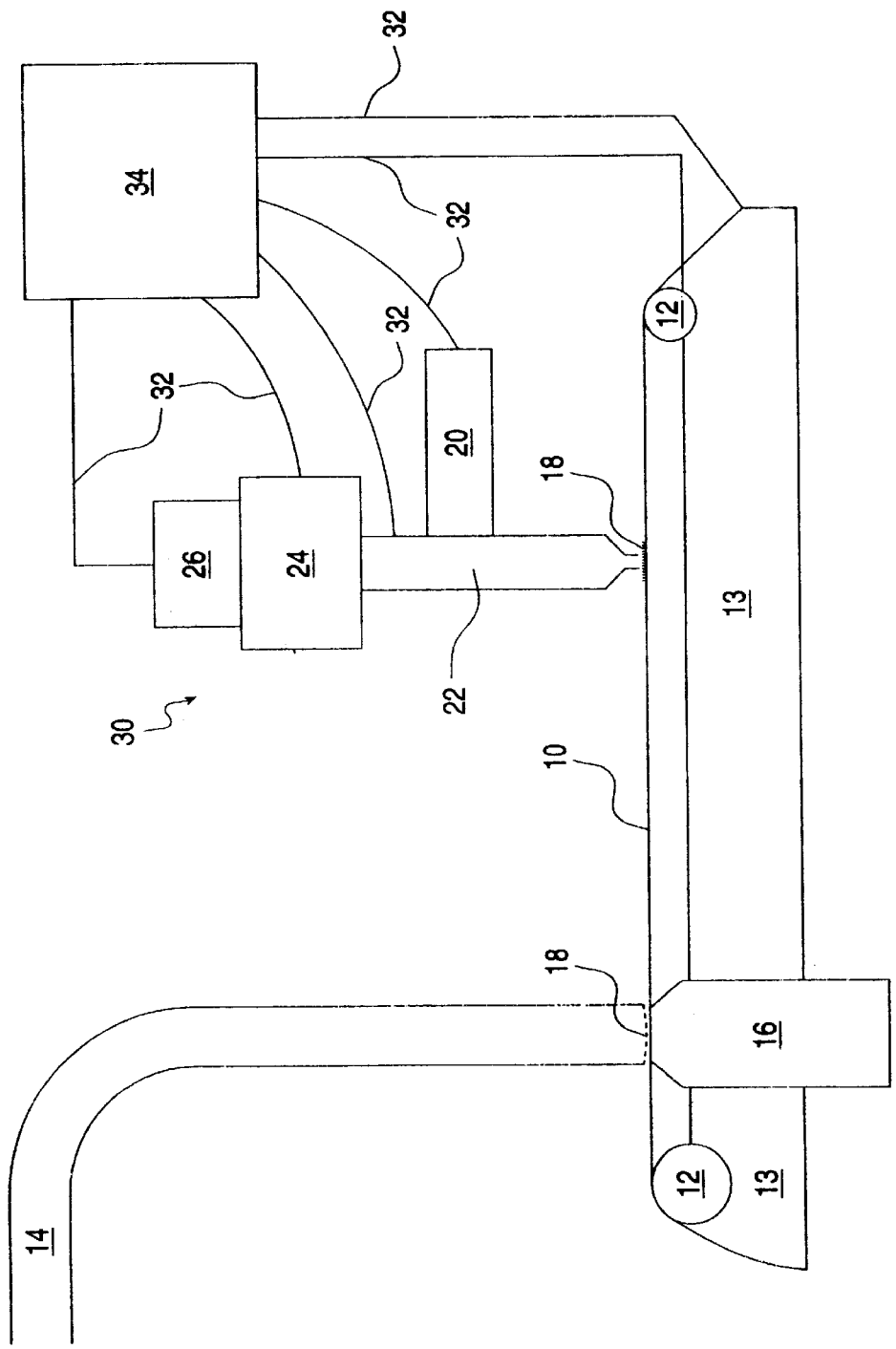
FIG. 1 is a schematic diagram of a system for quantifying PAH in aerosols.

Referring now to the drawings, FIG. 1 is a schematic diagram of an automatic on-line real-time system for monitoring PAH in aerosols. A roll of a non-fluorescing substrate 10 such as non-fluorescing filter paper is mounted on a pair of rollers 12, which move substrate 10 from left to right as seen in FIG. 1. A high volume air pump 16 sucks in contaminated air via a pipe 14 and through substrate 10, depositing aerosol particles 18 on substrate 10. Optionally, a filtration system (not shown), such as a 10PM high volume particle sampler, may be placed in pipe 14 to select particles below a certain size, for example, 10μ. Rollers 12 move aerosol articles 18 to a position for viewing under a spectroscopic imaging system 30 that includes a source of ultraviolet light 20, an optical system 22, a spectroscopic imaging device 24 and a CCD camera 26 having a suitable sensitivity and dynamic range. Typical spectroscopic imaging systems are described, for example, in the Lewis et al. patent cited above, and will not be elaborated further herein.

Components 20, 22, 24 and 26 of spectroscopic imaging system 30 are connected by suitable control/data links 32 to a control system 34. Light source 20 illuminates particles 18 homogeneously via optical system 22, as shown in FIGS. 6 and 8 of the Lewis et al. patent cited above. In other embodiments of the present invention, light source 22 directs ultraviolet light directly onto particles 18, without the intervention of optical system 22. Rollers 12 also are connected by a control/data link 32 to control system 34 so that substrate 10 can be advanced under the control of control system 34. Rollers 12 are mounted on a stage 13 which has two degrees of freedom of motion: laterally (into and out of the plane of FIG. 1) and vertically. The vertical motion of stage 13 is used to effect autofocusing. Stage 13 also is controlled by control system 34 via a control/data link 32. The combined motions of rollers 12 and stage 13 allow substrate 10 to be moved laterally in three directions under optical system 22.

Control system 34 is based on a personal computer, and includes a frame grabber, for acquiring images from camera 26, as well as other hardware interface boards for controlling rollers 12, stage 13 and the other components 20, 22 and 24 of spectroscopic imaging system 30. The software of control system 34 includes a database of empirically determined morphology types and spectrum type and code for implementing the image processing and quantification algorithms described below.

Preferably, rollers 12 are used to move substrate 10 to the right, as seen in FIG. 1, in a stepwise fashion, so that while control system 34 is acquiring and analyzing images of one sample of particles 18, pump 16 is collecting the next sample of particles 18. Rollers 12 and stage 13 also are used to move particles 18 a much shorter distance laterally under optical system 22, to allow control system 34 to acquire images from several fields of view in a sample.

Figure 2:
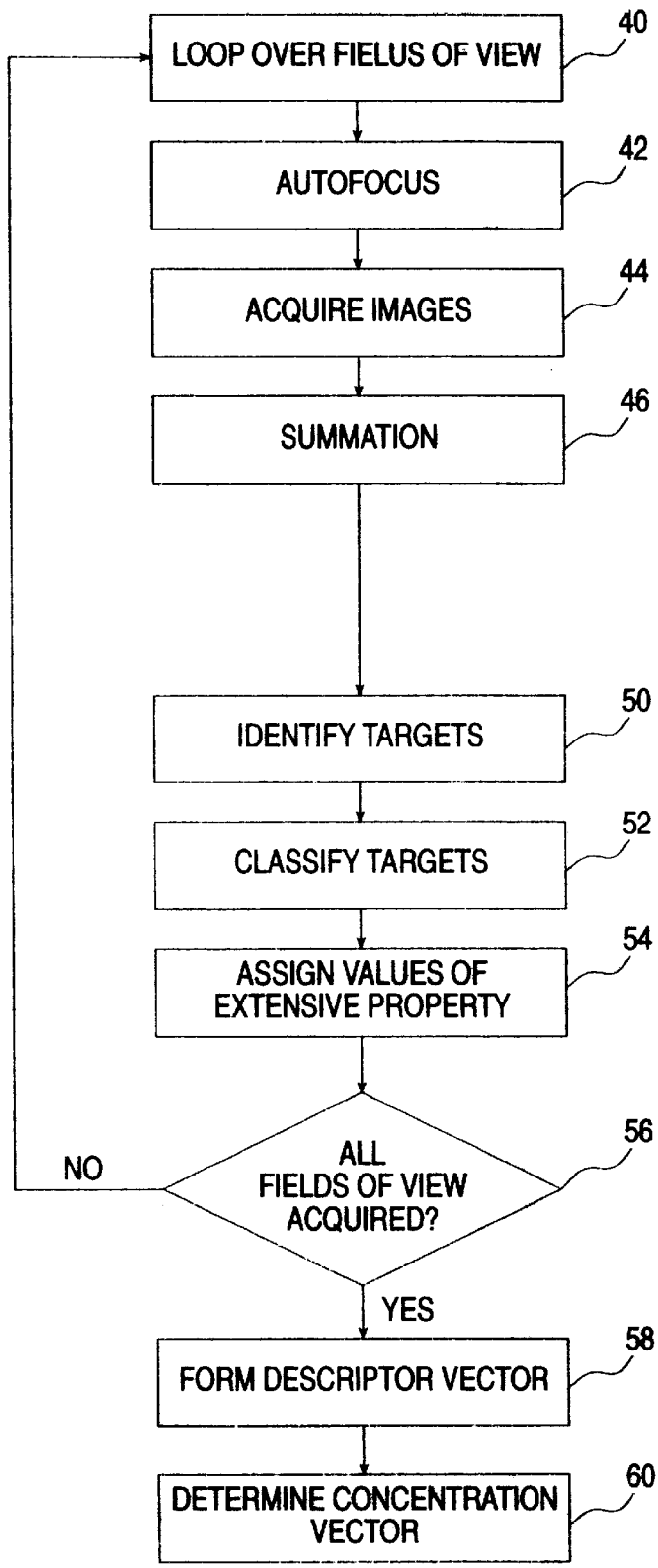
FIG. 2 is a flow diagram of the detection and quantification of PAH.

FIG. 2 is a flow diagram of the process of automatic detection and quantification of PAH. By shifting the field of view laterally, using rollers 12 and stage 13, images of all fields of view of the sample are acquired (blocks 40 and 56). Within each field of view, a set of images are acquired at the desired wavelengths (block 44) and the single-wavelength images are summed to give a summed, or gray level, image (block 46). Note that there is a one to one correspondence between the pixels of the summed image and what is referred to herein as the "common locations" of pixels of the single-wavelength images.

Subsequent image processing analyzes the images in terms of targets. Each target is a collection of pixels of single-wavelength images whose summed-image pixels have: (a) intensities above a preset threshold and (b) adjoining locations. The targets are identified (block 50) and classified (block 52), and each target is assigned a value of an extensive property (block 54).

The morphology types in the database are empirically determined ranges of parameters used to characterize the morphologies of the targets. For example, a set of targets could be described in terms of areas and aspect ratios, with three area ranges:

<5 square microns (small)

5–50 square microns (medium)

>50 square microns (large)

and two aspect ratio ranges:

1 to 1.5 (round)

>1.5 (elongated).

The cross-product of these ranges gives six morphology types: small round, small elongated, medium round, medium elongated, large round and large elongated. Raw morphology types may be merged to fewer types. For example, if the aspect ratios of small and large particles are of no consequence, the six raw morphology types may be merged to four: small ("sm"), medium round ("mr"), medium elongated ("me"), and large ("lg").

The spectrum types in the database are empirically determined normalized discrete functions of wavelength. Suppose that the single-wavelength images are acquired at L discrete wavelengths $\lambda_l$. Then each standard spectrum S is a collection of non-negative numbers $s_l$, one per wavelength, normalized as $$\sum_{l=1}^{L} S_l = 1 \qquad (1)$$

The target classes are direct products of the morphology types and the spectrum types. For example, if there are four morphology types (sm, mr, me and lg) and three spectrum types ($S_A$, $S_B$ and $S_C$) then there are twelve target classes.

There are two preferred methods for identifying targets (block 50) and classifying targets (block 52). The first method takes into account the spectra of the single-wavelength images, i.e., the intensities of the pixels at common locations. Suppose that at one location, the L pixels have intensities $p_l$. Each location whose summed intensity exceeds the threshold is classified by spectrum type, by seeking the spectrum type that most closely matches the location spectrum. One way of doing this matching is to take the dot product of the location spectrum with each of the spectrum types:

$$\sum_{l=1}^{L} p_l s_l^{\alpha}$$

where $\alpha$ indexes the spectrum type. The location is assigned the spectrum type whose dot product with the location spectrum is largest. Another way of doing this matching is to normalize the intensities $p_l$ to one, as in equation (1), and then to compute the squared Euclidean distance between the location spectrum and each of the spectrum types:

$$\sum_{l=1}^{L} (p_l - \bar{p} - s_l^{\alpha} + \bar{s}^{\alpha})^2,$$

where $\bar{p}$ is the mean of the $p_l$ and $\bar{s}^{\alpha}$ is the mean of the $s^{\alpha}_l$ for each $\alpha$. The location is assigned the spectrum type whose Euclidean distance from the location spectrum is smallest. Then, all adjoining locations of identical spectrum type are grouped together as targets.

The values of the parameters that define target morphology are computed by standard methods. For example, the area of a target is determined simply by counting the number of locations in the target; and the aspect ratio of a target is determined by finding the distance (length) between the two locations of the target that are farthest from each other, finding the maximum width of the target in the direction perpendicular to a line connecting those two pixels, and dividing the length by the width. Each target is assigned to the target class that corresponds to the values of the morphology parameters and the spectrum type that was used to define the target.

The second preferred method of identifying and classifying targets forms the targets by grouping together locations whose summed intensities exceed the threshold, without regard to location spectra. Then, within each target, each location's spectrum is classified by spectrum type as above, and a single representative spectrum type for the entire target is selected from among the matching spectrum types. The simplest way to select the representative spectrum type is by plurality: the spectrum type that is matched to the largest number of locations within the target is chosen as the representative spectrum type. The target morphology type is determined as in the first method, and the target is assigned to the target class that corresponds to the values of the morphology parameters and the representative spectrum type. Each target now is assigned a value of an extensive property such as target area or total target intensity (block 54).

After all fields of view have been processed (block 56), a descriptor vector d is formed (block 58) by summing the values of the extensive property of the targets of each class. The vector d has as many elements as there are target classes, and the elements of the vector d are the sums of the extensive property values of the targets of the corresponding target class. The last step (block 60) is to turn the descriptor vector into a concentration vector c whose elements are the concentrations, in mass per unit area, of the PAH species of interest. This is done using a relationship, determined by the calibration procedure described below, between the vectors d and c. If this relationship is determined by multivariate analysis, then the relationship is embodied in a matrix M such that c=dM. If this relationship is determined by training a neural net, then d is provided to the trained neural net as input, and c is the resulting output.

Another noteworthy difference between the present invention and the method of particulate analysis described in co-pending U.S. patent application Ser. No. 08/790,696 is that in the later patent application, only fields of view in which at least one target appears are considered. In the present invention, all fields of view are considered, in order to obtain correct statistics regarding the measured extensive property values.

Figure 3:
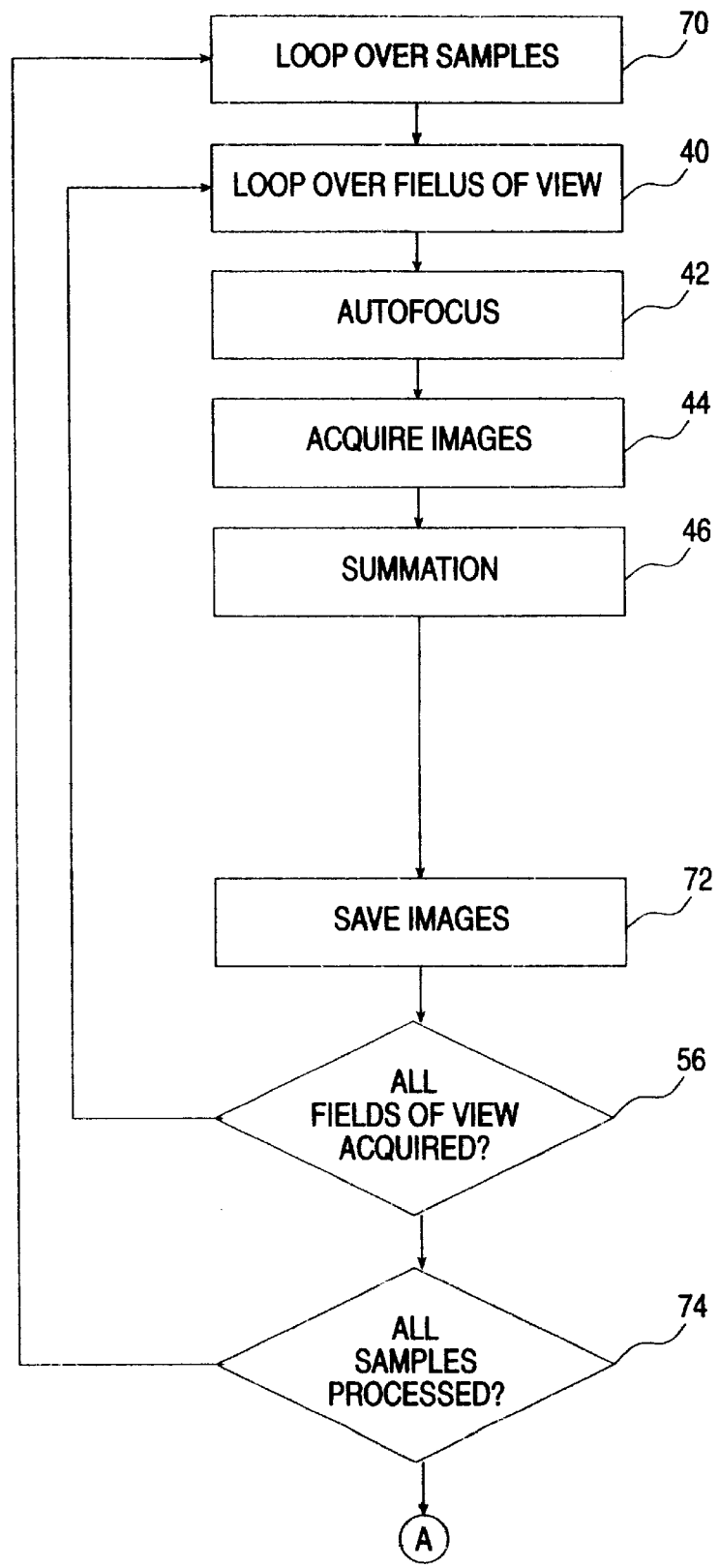
FIG. 3 is a flow diagram of the calibration of the quantification method
Figure 3:
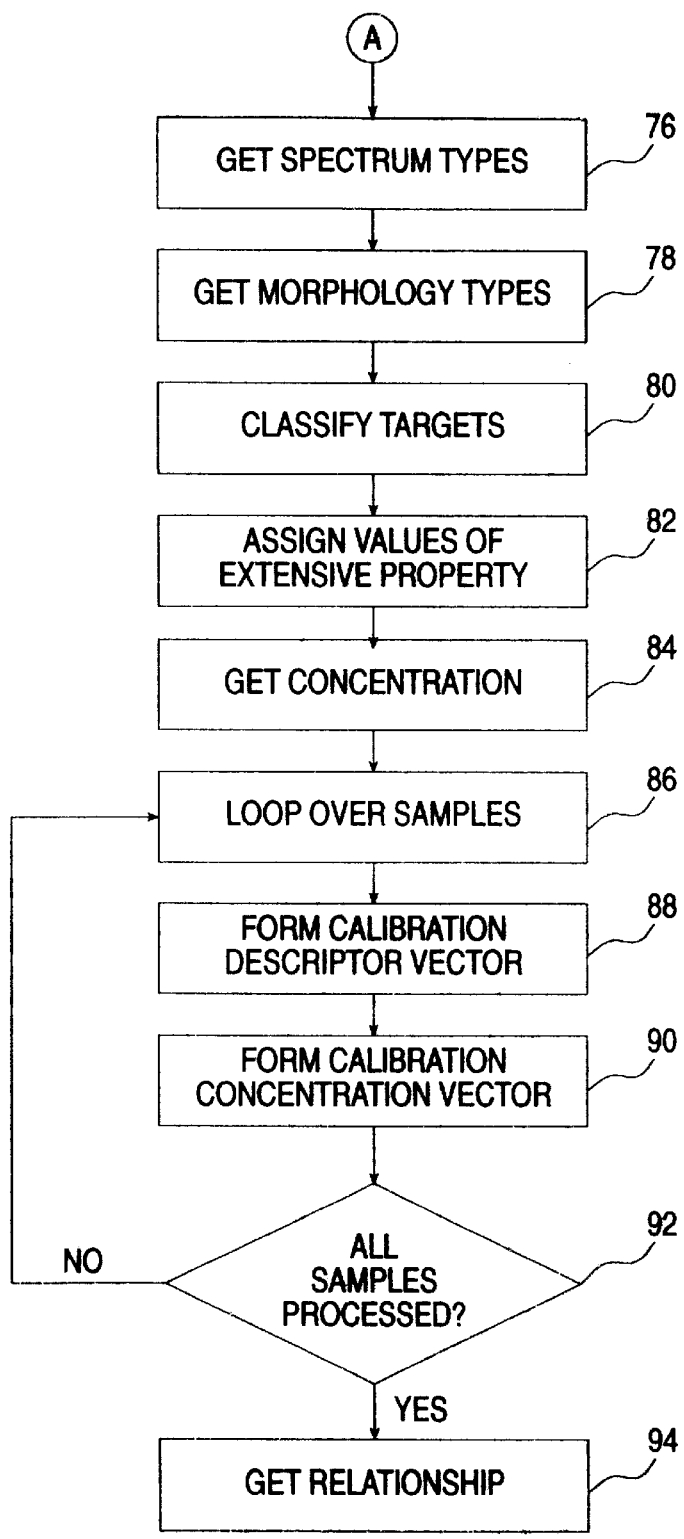

The process of FIG. 2 is calibrated using a set of N calibration samples, of the kind of particles that are to be analyzed. The calibration samples may be artificial samples of known composition or representative collections of particles, such as particles 18, that are to be analyzed. FIG. 3 is a flow diagram of the calibration procedure. The calibration procedure includes two loops over the N calibration samples. In the first loop, single-wavelength images of fields of view of the samples are acquired. Between the two loops, the database spectrum types and the database morphology types are determined. In the second loop, the relationship between descriptor vectors and concentration vectors is determined.

In the first loop (block 70), single-wavelength images of all fields of view of each sample are acquired as described above (blocks 40, 42, 44, 46 and 56). Images that include fluorescing particles are saved for subsequent processing (block 72). After all the relevant single-wavelength images of all the samples have been collected (block 74), the spectra of locations whose summed intensity exceeds the threshold are classified by cluster analysis to obtain the database spectrum types (block 76). Targets are identified as described above, the values of the morphology parameters of each target are computed, and the database morphology types are obtained by applying cluster analysis to the resulting set of morphology parameter values (block 78). The database morphology and spectrum types are used to define target classes, and the targets in all the fields of view of al the samples are classified according to these classes (block 80). Each target is assigned a value of an extensive property (block 82). If the calibration samples are artificial, then the concentrations of the PAH species of interest are known. If the calibration samples are representative collections, then, at the end of the first loop, each calibration sample is analyzed by a prior art (e.g., wet chemistry) technique to determine the concentrations therein of the PAH species of interest (block 84).

In the second loop over samples (block 86), for each sample, a calibration descriptor vector $d_n$ is formed (block 88) by summing the values of the extensive property of the targets of each class. ($n \in [1,N]$ is the index of the sample.) A calibration concentration vector $c_n$ is formed from the concentrations of the PAH species in the sample (block 90). After calibration descriptor vectors and calibration concentration vectors have been determined for all N calibration samples (block 92), a collective relationship between the descriptor vectors and the calibration vectors is determined (block 94). As noted above, under multivariate analysis this relationship is expressed as the matrix M that comes closest to giving $c_n = d_n M$ for all N samples. The simplest way to obtain M is by unweighted linear least squares. Form a matrix C whose rows are the vectors $c_n$. Form a matrix D whose rows are the vectors $d_n$. The desired matrix M should come close to satisfying the equation $$C = DM \tag{2}$$

The unweighted linear least squares solution of equation (2) for M is the generalized inverse solution for M. Multiplying both sides by the transpose of D, $D^T$, gives $$D^TC = D^TDM \quad (3)$$

The right hand side of equation (3) now is a product of M with a square matrix $D^TD$. Left-multiplying both sides of equation (3) by $(D^TD)^{-1}$ gives $$M = (D^TD)^{-1}D^TC \quad (4)$$

Other, more sophisticated methods of approximating M within the scope of multivariate analysis include principal component regression and partial least squares. See, for example, H. Martens and T. Naes, *Multivariate Calibration* (John Wiley & Sons, 1989).

Alternatively, a neural network is trained, using the calibration descriptor vectors and calibration concentration vectors as a training set. The desired relationship between descriptor vectors and concentration vectors then is the trained neural network. See, for example, P. Yu. V. Anastassopoulos and A. N. Venetsanopoulos, "Pattern classification and recognition based on morphology and neural networks", *Can. J Elect. and Comp. Eng.*, Vol. 17 No. 2 (1992) pp. 58–59 and the references therein.

As noted above, the scope of the present invention includes quantitation of both chemical species and biological species. The procedure described above for analysis of PAH on aerosol particles applies, *mutatis mutandis*, to analysis of airborne microorganisms. Such analysis is important in the control of indoor air pollution in environments, such as airports, with closed air circulation systems.

Figure 4A:
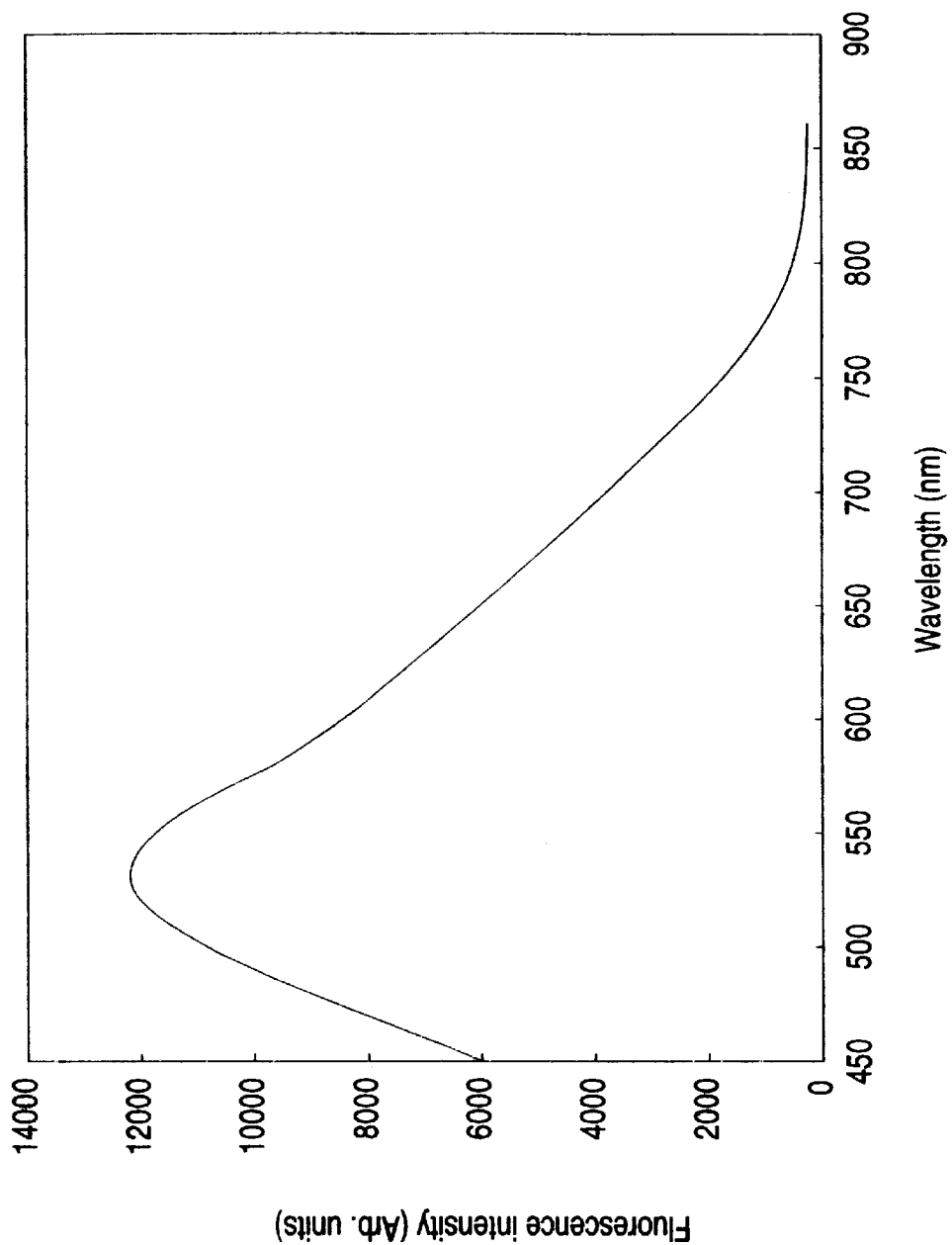
FIGS. 4A and 4B are fluorescence spectra of algal species.
Figure 4B:
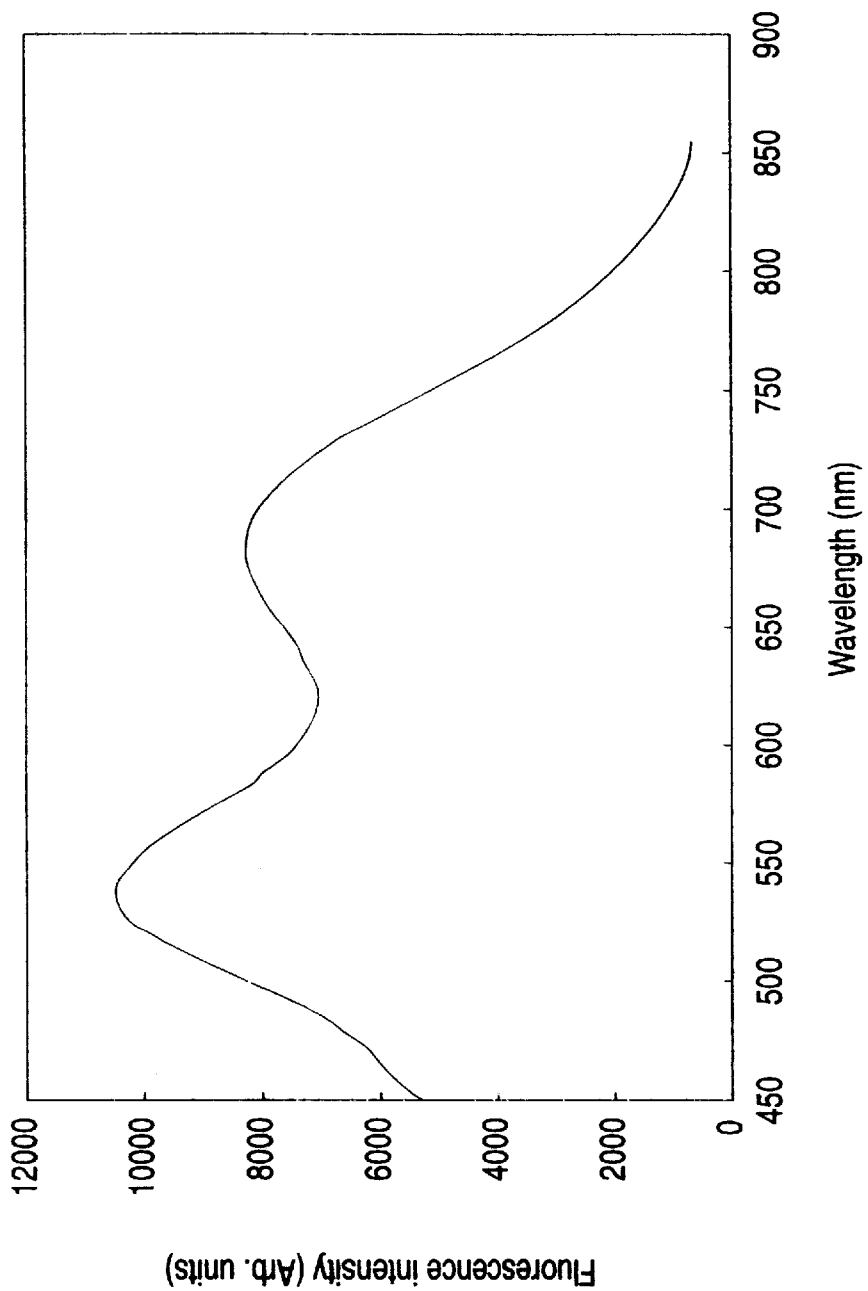

FIG. 4A shows the experimentally determined fluorescence spectrum, in arbitrary intensity units, of an algal species collected as airborne particulates. FIG. 4B shows the experimentally determined fluorescence spectrum, also in arbitrary intensity units, of another algal species, also collected as airborne particulates. The spectrum of FIG. 4B has two peaks, at about 520 nm and about 675 nm, corresponding to juvenile and mature members of the species. Such spectra can be used for the classification of airborne microorganisms in the same way that chemical fluorescence spectra can be used to classify chemical species on aerosol particles.

While the invention has been described with respect to a limited number of embodiments, it will be appreciated that many variations, modifications and other applications of the invention may be made.

What is claimed is:

1. A method of analyzing particles for a plurality of species, comprising the steps of:

(a) providing:
  (i) a plurality of morphology types;
  (ii) a plurality of spectrum types;
  (iii) a plurality of target classes, each of said target classes corresponding to one of said morphology types and one of said spectrum types, and
  (iv) a relationship between a descriptor vector and a concentration vector, said descriptor vector including a plurality of elements, each element of said descriptor vector corresponding to a different one of said target classes, said concentration vector including a plurality of elements, each element of said concentration vector corresponding to a different one of the species;
(b) acquiring a plurality of images of the particles, each of said images being acquired at a different wavelength;
(c) inferring said descriptor vector from said plurality of images; and
(d) using said relationship to infer said concentration vector from said descriptor vector.

2. The method of claim 1, wherein said acquiring of said images is effected using a scanning interferometer.

3. The method of claim 1, wherein said acquiring of said images is effected using a liquid crystal tunable filter.

4. The method of claim 1, wherein said acquiring of said images is effected using an acousto-optic tunable filter.

5. The method of claim 1, wherein said acquiring of said images is effected using a spectrometer.

6. The method of claim 1, wherein said inferring of said descriptor vector from said plurality of images includes the steps of:

(i) identifying a plurality of targets in said plurality of images;
(ii) for each of said targets:
  (A) associating said each target with one of said target classes, and
  (B) obtaining a value of an extensive property of said each target;
(iii) for each of said target classes, summing said values of said extensive property of said targets associated with said each target class to obtain said element of said descriptor vector that corresponds to said target class.

7. The method of claim 6, wherein each of said images includes a plurality of pixels, each of said pixels having a location in said each image, each of said pixels having an intensity, and wherein said identifying of said plurality of targets includes the step of:

(A) for each of said locations, summing said intensities of said pixels that have said each location, thereby obtaining a summed intensity.

8. The method of claim 7, wherein said identifying of said plurality of targets further includes the steps of:

(B) for each of said locations for which said summed intensity exceeds a threshold: matching said intensities of said pixels having said each location to one of said spectrum types, thereby obtaining a matched spectrum type; and
(C) for each said matched spectrum type, grouping adjoining said locations that share said each matched spectrum type, thereby obtaining one of said targets.

9. The method of claim 8, wherein said associating of said each target with one of said target classes includes the steps of:

(I) determining at least one morphological parameter of said each target; and
(II) matching said at least one morphological parameter with one of said morphology types, thereby obtaining a matched morphology type;

said each target then being associated with said target class corresponding to said matched spectrum type and said matched morphology type.

10. The method of claim 7, wherein said identifying of said plurality of targets further includes the step of:

(B) grouping adjoining said locations for which said summed intensity exceeds a threshold to obtain one of said targets.

11. The method of claim 10, wherein said associating of said each target with one of said target classes includes the steps of:

(I) determining at least one morphological parameter of said each target;
(II) matching said at least one morphological parameter with one of said morphology types, thereby obtaining a matched morphology types;
(III) for each location in said each target, matching said intensities of said pixels having said each location to one of said spectrum types, thereby obtaining a matched spectrum type; and (IV) selecting, from among said matched spectrum types, a representative spectrum type;

said each target then being associated with said target class corresponding to said representative spectrum type and said matched morphology type.

12. The method of claim 1, wherein said providing of said plurality of morphology types is effected by steps including:

(A) providing at least one calibration sample of the particles;

(B) for each of said at least one calibration sample:
  (I) acquiring a plurality of calibration images of the particles of said each calibration sample, each of said calibration images being acquired at a different wavelength,
  (II) identifying a plurality of calibration targets in said plurality of calibration images, and
  (III) for each of said plurality of calibration targets: determining at least one morphological parameter; and (C) performing cluster analysis on said at least one morphological parameter of said calibration targets of said at least one calibration sample.

13. The method of claim 1, wherein said providing of said plurality of spectral types is effected by steps including:

(A) providing at least one calibration sample of the particles;

(B) for each of said at least one calibration sample:
  (I) acquiring a plurality of calibration images of the particles of said each calibration sample, each of said calibration images being acquired at a different wavelength, each of said calibration images including a plurality of pixels, each of said pixels having a location in said each calibration image, each of said pixels having an intensity, and
  (II) for each of said locations, summing said intensities of said pixels that have said each location, thereby obtaining a summed intensity; and (C) performing cluster analysis on said intensities of said pixels of said locations whose summed intensity exceeds a threshold.

14. The method of claim 1, wherein said providing of said relationship between said descriptor vector and said concentration vector is effected by steps including:

(A) providing at least one calibration sample of the particles;

(B) for each of said at least one calibration sample:
  (I) acquiring a plurality of calibration images of the particles of said each calibration sample, each of said calibration images being acquired at a different wavelength,
  (II) inferring a calibration descriptor vector from said plurality of images, said calibration descriptor vector including a plurality of elements, each element of said descriptor vector corresponding to a different one of said target classes,
  (III) analyzing said each calibration sample to obtain a concentration of each of the species, and
  (IV) forming a calibration concentration vector, said calibration concentration vector including a plurality of elements, each element of said calibration concentration vector being a different one of said concentrations; and (C) inferring said relationship from said calibration descriptor vectors and from said calibration concentration vectors.

15. The method of claim 14, wherein said inferring is effected by multivariate analysis.

16. The method of claim 14, wherein said inferring is effected by training a neural net.

17. The method of claim 1, wherein said providing of said relationship between said descriptor vector and said concentration vector is effected by steps including:

(A) providing at least one calibration sample of the particles for which concentrations of the species are known;

(B) for each of said at least one calibration sample:
  (I) acquiring a plurality of calibration images of the particles of said each calibration sample, each of said calibration images being acquired at a different wavelength,
  (II) inferring a calibration descriptor vector from said plurality of images, said calibration descriptor vector including a plurality of elements, each element of said descriptor vector corresponding to a different one of said target classes, and
  (IV) forming a calibration concentration vector, said calibration concentration vector including a plurality of elements, each element of said calibration concentration vector being a different one of said concentrations; and (C) inferring said relationship from said calibration descriptor vectors and from said calibration concentration vectors.

18. The method of claim 17, wherein said inferring is effected by multivariate analysis.

19. The method of claim 17, wherein said inferring is effected by training a neural net.

20. The method of claim 1, wherein said relationship is linear.

21. The method of claim 1, wherein said relationship is implemented as a neural net.

22. The method of claim 1, wherein said acquiring of said plurality of images is effected by steps including exciting the particles to emit emitted light, each of said images being of said emitted light.

23. The method of claim 22, wherein said exciting is effected by directing excitation light at the particles.

* * * * *